US005769890A

United States Patent [19]

McDonald

[11] Patent Number: 5,769,890
[45] Date of Patent: Jun. 23, 1998

[54] PLACEMENT OF SECOND ARTIFICIAL LENS IN EYE, TO CORRECT FOR OPTICAL DEFECTS OF FIRST ARTIFICIAL LENS IN EYE

[75] Inventor: Henry H. McDonald, 525 E. Cordova St., #100, Pasadena, Calif. 91101

[73] Assignees: Henry H. McDonald; William H. Haefliger, Pasadena, Calif.; a part interest

[21] Appl. No.: 786,368

[22] Filed: Jan. 16, 1997

[51] Int. Cl.⁶ ........................................................ A61F 2/16
[52] U.S. Cl. ............................................... 623/6; 606/107
[58] Field of Search .................................. 623/6; 606/107

[56] References Cited

U.S. PATENT DOCUMENTS

| 4,573,998 | 3/1986 | Mazzocco | 623/6 |
|---|---|---|---|
| 4,585,456 | 4/1986 | Blackmore | 623/6 |
| 4,605,409 | 8/1986 | Kelman | 623/6 |
| 4,731,078 | 3/1988 | Stoy et al. | 623/6 |
| 4,759,761 | 7/1988 | Portnoy | 623/6 |
| 4,769,035 | 9/1988 | Kelman | 623/6 |
| 4,813,957 | 3/1989 | McDonald | 623/6 |
| 4,833,890 | 5/1989 | Kelman | 623/6 |
| 4,840,627 | 6/1989 | Blumenthal | 623/6 |
| 4,888,014 | 12/1989 | Nguyen | 623/6 |
| 4,907,586 | 3/1990 | Bille et al. | 606/5 |
| 4,932,970 | 6/1990 | Portney | 623/6 |
| 4,932,971 | 6/1990 | Kelman | 623/6 |
| 4,950,288 | 8/1990 | Kelman | 623/6 |
| 4,955,902 | 9/1990 | Kelman | 623/6 |
| 4,957,505 | 9/1990 | McDonald | 623/6 |
| 4,959,070 | 9/1990 | McDonald | 623/6 |
| 5,019,091 | 5/1991 | Knight et al. | 623/5 |
| 5,030,231 | 7/1991 | Portney | 623/6 |
| 5,044,743 | 9/1991 | Ting | 351/163 |
| 5,098,444 | 3/1992 | Feaster | 623/6 |
| 5,203,789 | 4/1993 | McDonald | 623/6 |
| 5,203,790 | 4/1993 | McDonald | 623/6 |
| 5,258,025 | 11/1993 | Fedorov et al. | 623/6 |
| 5,292,324 | 3/1994 | McDonald | 606/107 |
| 5,480,428 | 1/1996 | Fedorov et al. | 623/6 |

FOREIGN PATENT DOCUMENTS

| 1477109 | 3/1992 | European Pat. Off. | 623/6 |
|---|---|---|---|
| 2666735 | 3/1992 | France | 623/6 |
| 034325 | 7/1958 | Germany | 623/6 |
| 4129668 | 5/1992 | Germany | 623/6 |
| 1168238 | 7/1985 | U.S.S.R. | 106/107 |
| WO8902252 | 3/1989 | WIPO . | |
| WO911359 | 9/1991 | WIPO . | |
| 9220302 | 11/1992 | WIPO | 623/6 |
| 9303776 | 3/1993 | WIPO | 623/6 |

*Primary Examiner*—Mary Beth Jones
*Attorney, Agent, or Firm*—William W. Haefliger

[57] ABSTRACT

The method of providing corrected vision in an eye wherein a first artificial lens has been previously placed in the lens capsule of the eye, which includes providing a second artificial lens to have opposed surfaces, and inserting the second lens in an eye chamber forward of the capsule so that one of the opposed surfaces faces toward the first lens, the second lens characterized as correcting for optical defects associated with the first lens.

11 Claims, 3 Drawing Sheets

PLACEMENT OF SECOND ARTIFICIAL LENS IN EYE, TO CORRECT FOR OPTICAL DEFECTS OF FIRST ARTIFICIAL LENS IN EYE

BACKGROUND OF THE INVENTION

This invention relates generally to improving vision in an eye containing an artificial lens, and more particularly concerns providing a second artificial lens in the eye having optical characteristics cooperating with those of the first lens to produce good vision.

When an artificial lens is implanted in the capsule of the eye, it sometimes happens that vision is not improved to the degree as was expected, due to characteristics of the implant. Such lens implant usually follows a cataract extraction procedure. For example, the lens implant may be aphakic. There can be a strong demand for sufficient correction of these refractive errors, so strong that patients want the erroneous lens implants to be extracted, which can be very dangerous.

There is need for a simple procedure which will correct this undesired condition, and will result in good vision, without involving extraction of the errant first lens implant.

SUMMARY OF THE INVENTION

It is a major object of the invention to provide a procedure or method, as well as a means, for meeting the above need.

Basically, the method of the invention involves the steps:
a) providing a second artificial lens to have opposed surfaces,
b) and inserting the second lens into the eye posterior chamber between the iris and the lens capsule so that one of the opposed surfaces faces toward the first lens,
c) the second lens characterized as correcting for optical defects associated with the first lens.

As will be seen, one surface of the second inserted lens is typically positioned to be concave toward the first lens, and the second lens is inserted into the eye to extend proximate the first lens and intermediate the cornea and the first lens.

Another object is to employ a secondary lens implant whose posterior surface conforms to the anterior surface of an initially inserted aphakic lens implant. The secondary lens implant also has a corrective dioptric power necessary to achieve a desired refractive value for refractive errors of myopia, hyperopia, and astigmatism and even for anisometropia, and mechanical ability to correct for excess mydriasis.

A secondary benefit, so desirable for elderly seniors and aphakicly lens implanted patients, is that of achieving significant improvement in accommodation that does not exist in up to 99% of these patients.

A further object is to provide strand-like haptics attached to the second lens and characterized by one of the following:
i) the haptics project substantially parallel to the iris,
ii) the haptics have root ends projecting from edges of said second lens, in the posterior chamber,
iii) the haptics extend substantially perpendicular to haptics attached to the first lens.

Yet another object of the method is to first insert the secondary lens into the anterior chamber of the eye, and maneuvering the second lens through the eye pupil area into the posterior chamber, wherein it may also be rotated. As will be seen, the second lens may for example consist of a soft, compliant lens.

A further object is to provide a method wherein one the two lenses has haptics variably constrained by eye muscle induced movement, to variably displace the one lens, axially, and relative to the other of the two lenses.

These and other objects and advantages of the invention, as well as the details of an illustrative embodiment, will be more fully understood from the following specification and drawings, in which:

DRAWING DESCRIPTION

DETAILED DESCRIPTION

Figure 1:
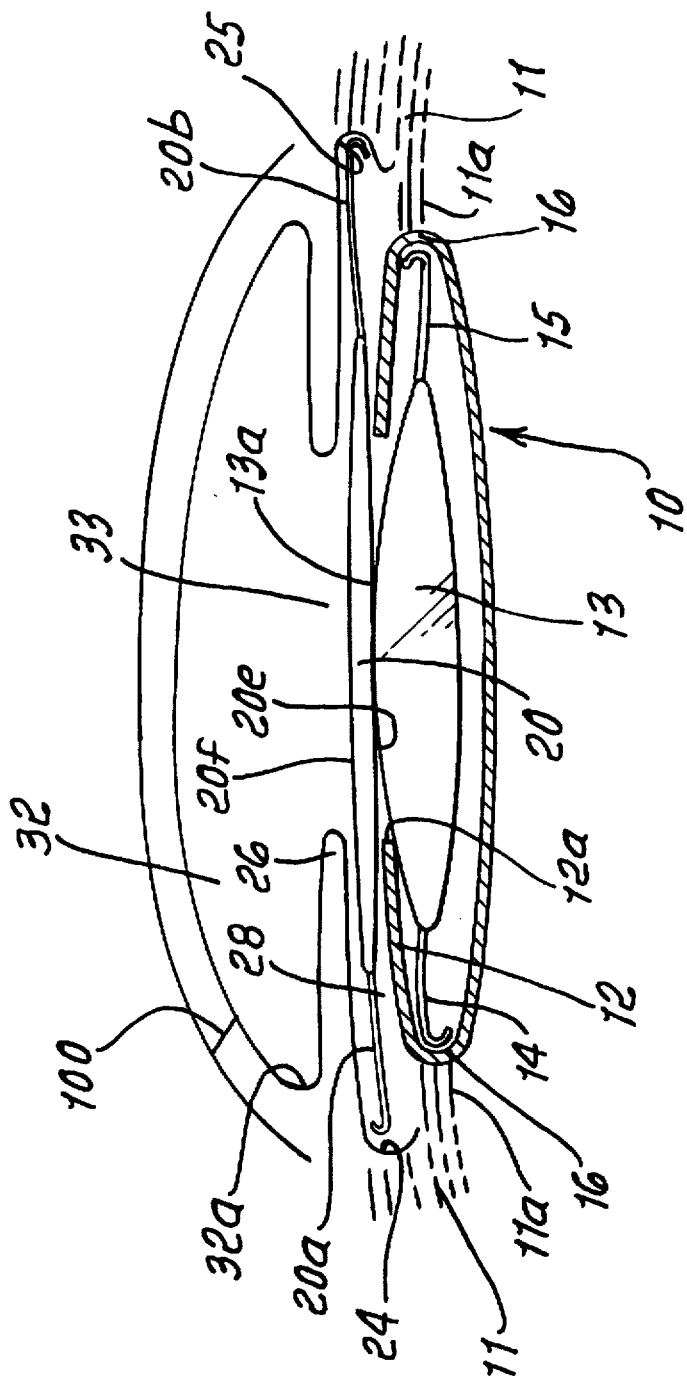
FIG. 1 is a view taken in section through the eye.
Figure 2:
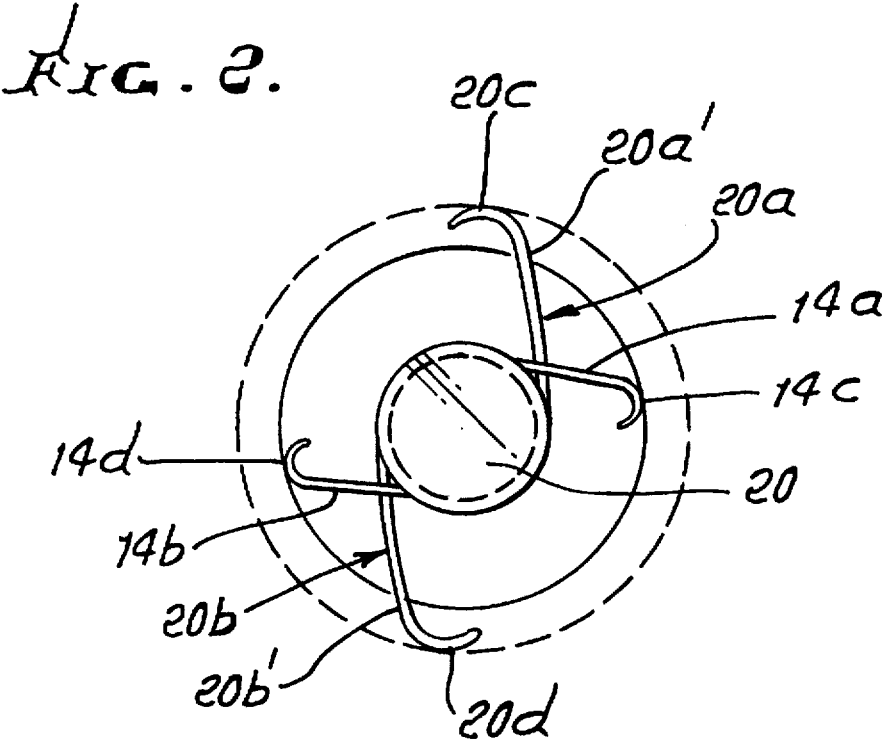
FIG. 2 is a view taken along the optical axis to show the relative positions of the two lenses and their haptics.

Referring first to FIG. 1, the natural lens capsule, from which the natural lens material has been removed, is indicated generally at 10. It is attached at 11a to ciliary muscles 11. A frontal opening 12a is cut or formed in the front wall 12 of the capsule to allow insertion or implanting of a first artificial lens 13. Haptics 14 and 15 of lens 13 extend to the inner surface of the capsule peripheral wall 16, as shown, to centrally position the lens. See also FIG. 2 showing legs 14a and 15a of such haptics.

Also shown in FIG. 1 is a second artificial lens 20 having opposed surfaces 20e and 20f. Surface 20e is preferably concave toward the first artificial lens 13, and is inserted in the eye so that surface 20e extends proximate the convex surface 13a of the first lens, at the capsulary opening 12a. The second lens is characterized, or formed, so as to correct for optical deflects associated with the implanted first lens, whereby the combined optical properties of the first and second lenses disposed in "piggy-back" relation result in good or desired vision. Note the compliant concave surface of lens 20 adjacent and conforming to the forward convex surface of lens 13.

In this regard, the corrective second lens 20 corrects for the in-place optical deficiencies or errors of the first lens, however those errors may have arisen. One example would be that the first lens may have become slightly distorted after extended use in the eye. Distortion might arise due to changes in physical properties of the synthetic material of the lens, or physical changes in the surrounding tissue.

The second lens has positioning haptics 20a and 20b that extend in posterior chamber 28 from the periphery of lens 20 to the sulcus inner surfaces 24 and 25, as shown, thereby centering the lens 20, and assisting its positioning between the iris 26 and the first lens 13. Haptics legs 20a' and 20b' are also seen in FIG. 2, and desirably are positioned to extend in substantially perpendicular superimposed relation to the respective legs 14a and 14b, for optimum relative positioning of the two lenses. The leg 20a' extends within an angular section zone angularly closer to leg 14a than to leg 14b; and leg 20b' extends within an angular section zone angularly closer to leg 14b than to leg 14a. Lenses 13 and 20 are substantially coaxial and may be relatively rotated into correct position. Curved outer stabilizing portions of the haptics are seen at 14c and 14d, and 20c and 20d, to engage the walls 16 and 24.

Accordingly, the method of the invention basically includes the steps a) providing a second artificial lens to have opposed surfaces, b) and inserting the second lens into the eye posterior chamber between the iris and the capsule so that one of the opposed surfaces of the second lens faces toward the first lens, c) the second lens characterized as correcting for optical defects associated with the first lens.

In this regard, the implantation step typically includes inserting the second lens into the anterior chamber of the eye, and maneuvering the second lens through the eye pupil area into the posterior chamber. The anterior chamber appears at 32 and the pupil area at 33. Also, the second lens typically consists of soft, compliant synthetic resinous material. Examples are collamer, silicon, and acrylic material. A small slit 100 in the eye will allow folded lens insertion into chamber 32, and unfolding therein. If desired, the lens 20 can be positioned in anterior chamber, with haptic ends 20c and 20d engaging wall 32a.

Also, the selection of the second lens typically includes the steps of determining the diopter characteristics of the first lens in the eye as having a quantitative difference from a desired diopter characteristic associated with good vision, and using said quantitative difference to impart a diopter characteristic to the second lens such that the combined diopter characteristics of the first and second lenses produce good vision. The second lens can be rotated in the posterior chamber, relative to the first lens, into position wherein the combined diopter characteristics of the first and second lenses produce good vision. This is done to correct for astigmatism, where the second lens has different diopter powers at different quadrants. The measurement of the first lens diopter characteristics may be carried out as by conventional optometric vision testing. See also the lens configuration determination in U.S. Pat. No. 4,769,035.

Figure 3:
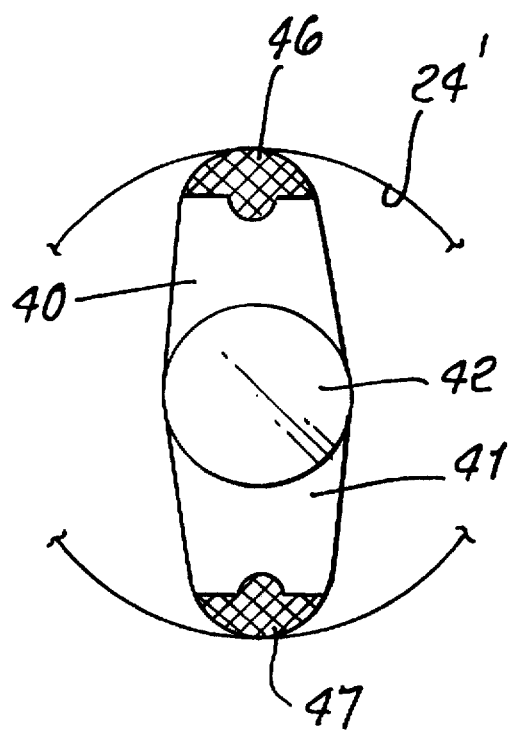
FIG. 3 is a plan view of an alternative lens.

An additional aspect concerns the provision of alternative plate like haptics 40 and 41 for a lens 42, as in FIG. 3, where the latter may be used with such tabular or plate-like haptics for either or both of the two lenses 10 and 20. Perforated, arcuate mesh regions 46 and 47 on 40 and 41 at haptic peripheries allow formation of eye tissue adhesions, to stabilize and locate 40 and 42, in the eye. The haptics engage the chamber interior wall 24'.

Figure 4:
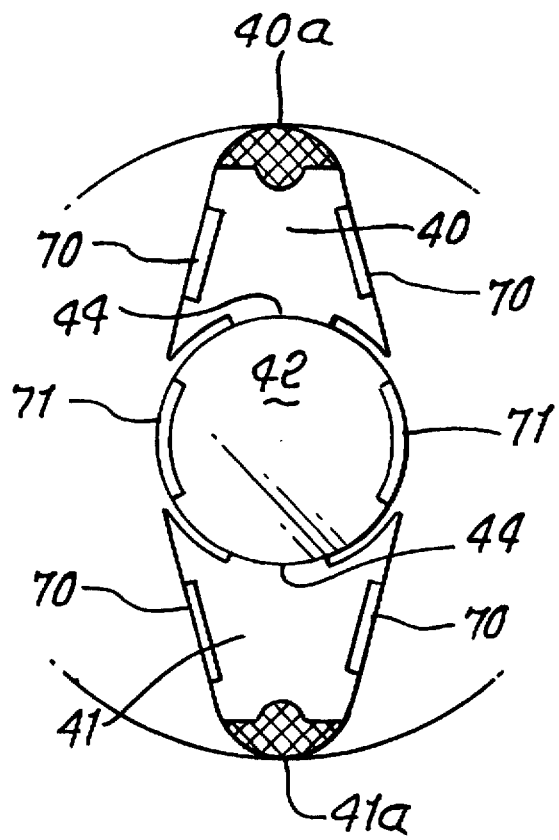
FIG. 4 is a plan view of yet another modified lens.

Such haptics 40 and 41 may be hingedly operatively connected to lens 42, as at narrowed hinge region 44 in FIG. 4, so that lens 42 in the capsule moves forwardly and rearwardly in conjunction with changes in position of the ciliary muscles 11, as where lens 42 is used for lens 13.

The haptics 40 and 41 may consist of molded synthetic resinous material, such as polypropylene. Filament type haptics as in FIG. 2 may hinge, for the same purpose.

When passively relaxed, the ciliary muscle (to which this mesh has adhesion) is less constricted in pulling away from the center of the optical segment. When the muscle is more constricted, as in response to the brain's desire to focus closer, the direct pressure on the haptic periphery focuses the optic segment forwardly to increase the curvature of the lens leading to effecting of "+" dioptric power. This effect is more pronounced during use of a soft lens such as is characteristic of a collamer lens.

Figure 5:
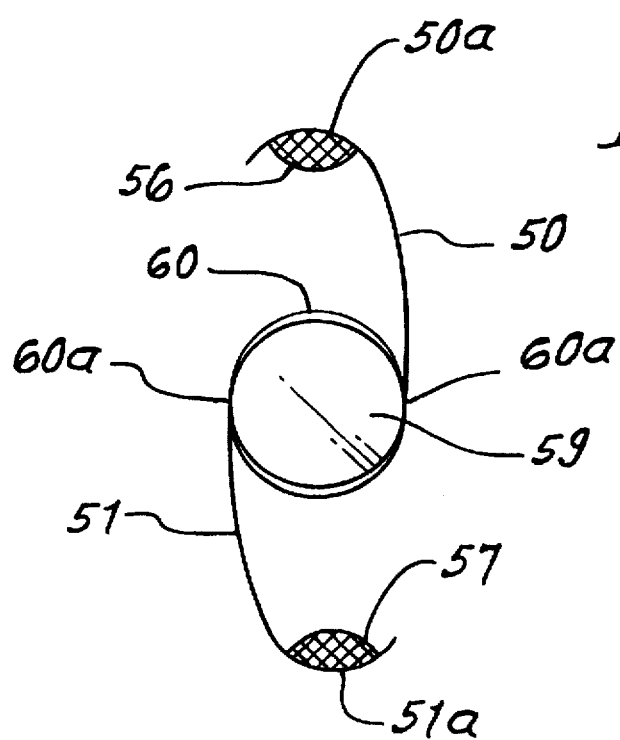
FIG. 5 is a plan view of a further modification.

Tabular zones 40 and 41 in FIG. 4 are made relatively stiff, and lens 42 may be made relatively thin. Note outwardly convexly curved peripheral surfaces at 40a and 41a. FIG. 5 shows a lens 59 having filamentary type haptics 50 and 51 with curved outer portions 50a and 51a. Mesh regions 56 and 57 are provided at outer portions 50a and 51a, as shown. Lens 59 has peripheral skeletal structure 60, thinned at 60a, for hinging attachment to the haptics, allowing lens movement as in FIG. 4. In FIGS. 3 and 4 lens edges and tabular haptic edges may have skeletal strengthening as at 70 and 71.

Either of the lenses may be triple folded into very small M or W shape, for insertion through a very small slit in the eye wall, one example being slit 100. Use of collamer lens material facilitates such multiple folding. See my U.S. patent application Ser. No. 08/680,683, incorporated herein by reference, wherein triple folding of the lens accommodates locating mutually compacted elements of the second lens in side-by-side stacked and sandwiched relation, prior to inserting thereof into the eye. The M-shape folded lens is allowed to resiliently unfold in the anterior chamber, and then maneuvered into the posterior chamber, or unfolded in the posterior chamber.

Other type useful lenses are described in my U.S. Pat. No. 5,203,789.

From the foregoing it will be seen that the first and second lens each have haptics attached thereto, said maneuvering of the second lens effected to position the haptics of the second lens in generally perpendicular superimposed relation to the haptics of the first lens; also that the second lens is provided with haptics that remain hingedly operatively attached thereto after completion of said inserting into said eye chamber; also, that the second lens is allowed freedom to move relative to the first lens, in said eye chamber, after completion of said inserting.

I claim:

1. The method of providing corrected vision in an eye wherein a first artificial lens including haptics has been previously placed in the lens capsule of the eye, which includes:

a) providing a second artificial lens to have opposed surfaces, the second lens also having haptics, b) and inserting said second lens in an eye chamber forward of said capsule and generally rearward of the eye iris and pupil area so that one of said opposed surfaces faces toward said first lens, and so that the second lens remains rotatable relative to the first artificial lens, c) the second lens characterized as correcting for optical defects associated with the first lens, d) and orienting the second lens haptics to be out of alignment with the first lens haptics.

2. The method of claim 1 which includes providing said surfaces so that said one surface of the second lens is concave toward said first lens.

3. The method of claim 1 wherein said one surface of the second lens is inserted to extend proximate said first lens and intermediate the cornea and said first lens.

4. The method of claim 1 including inserting said second lens into the anterior chamber of the eye, and maneuvering the second lens through the eye pupil area into said posterior chamber.

5. The method of claim 4 including preliminary triple folding said second lens into M shape, which is then inserted via a small slit into the eye posterior chamber, to resiliently unfold therein, said preliminary triple folding accommodates locating of mutually compacted elements of the second lens in side-by-side stacked and sandwiched relation, prior to inserting into the eye.

6. The method of claim 1 wherein said second lens is a soft, compliant lens.

7. The method of claim 1 including determining the diopter characteristics of the first lens in the eye as having a quantitative difference from a desired diopter characteristic associated with good vision, and using said quantitative difference to impart a diopter characteristic to the second lens such that the combined diopter characteristics of the first and second lenses produce good vision.

8. The method of claim 7 wherein said second lens consists of one of the following:

i) collamer, ii) silicon, iii) acrylic material, iv) synthetic resin.

9. The method of claim 1 including rotating said second lens in said posterior chamber relative to said first lens, into position wherein the combined diopter characteristics of the first and second lenses produce good vision.

10. The method of claim 1 wherein said first and second lens each have haptics attached thereto, said maneuvering of the second lens effected to position the haptics of the second lens in generally perpendicular superimposed relation to the haptics of the first lens.

11. The method of claim 1 including allowing the second lens freedom to move relative to the first lens, in said eye chamber.

* * * * *

REEXAMINATION CERTIFICATE (4149th)

United States Patent [19]
McDonald

[11] B1 5,769,890
[45] Certificate Issued Sep. 5, 2000

[54] PLACEMENT OF SECOND ARTIFICIAL LENS IN EYE, TO CORRECT FOR OPTICAL DEFECTS OF FIRST ARTIFICIAL LENS IN EYE

[75] Inventor: Henry H. McDonald, Pasadena, Calif.

[73] Assignee: Surgical Concepts, Inc., Newport Beach, Calif.

Reexamination Request:
No. 90/005,396, Jul. 8, 1999

Reexamination Certificate for:
Patent No.: 5,769,890
Issued: Jun. 23, 1998
Appl. No.: 08/786,368
Filed: Jan. 16, 1997

[51] Int. Cl.[7] .................................. A61F 2/16
[52] U.S. Cl. .................................. 623/6.34; 606/107
[58] Field of Search ................ 623/6, 6.32, 6.34

[56] References Cited

U.S. PATENT DOCUMENTS 4,573,998  3/1986  Mazzocco ........................... 623/6
5,098,444  3/1992  Feaster ............................... 623/6

OTHER PUBLICATIONS

"Polyseudophakia" by Harry B. Grabow published Jul., 1977, pp. 1–6.

"Achieving Emmetropia in Extremely Short Eyes With Two Piggyback Posterior Chamber Intraocular Lenses", by Jack T. Holladay et al, published in "Ophthalmology", vol. 103, No. 7 Jul., 1996, pp. 1118–1123.

*Primary Examiner*—David Willse

[57] ABSTRACT

The method of providing corrected vision in an eye wherein a first artificial lens has been previously placed in the lens capsule of the eye, which includes providing a second artificial lens to have opposed surfaces, and inserting the second lens in an eye chamber forward of the capsule so that one of the opposed surfaces faces toward the first lens, the second lens characterized as correcting for optical defects associated with the first lens.

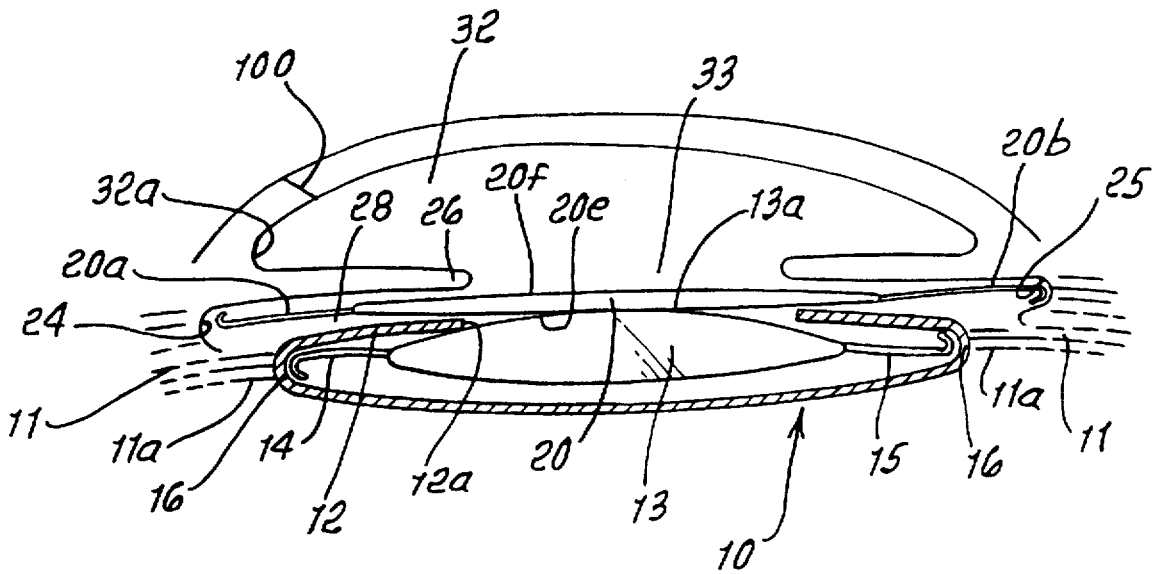

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 3–13:

In this regard, the implantation step typically includes inserting the second lens into the anterior chamber of the eye, and maneuvering the second lens through the eye pupil area into the posterior chamber. The anterior chamber appears at 32 and the pupil area at 33. Also, the second lens typically consists of soft, compliant synthetic resinous material. Examples are collamer, [silicon] *silicone*, and acrylic material. A small slit 100 in the eye will allow folded lens insertion into chamber 32, and unfolding therein. If desired, the lens 20 can be positioned in anterior chamber, with haptic ends 20c and 20d engaging wall 32a.

AS A RESULT OF REEXAMINATION, IT HAS BEEN DETERMINED THAT:

The patentability of claims 1, 2, 4–7, 9 and 11 is confirmed.

Claims 3, 8 and 10 are determined to be patentable as amended.

New claim 12 is added and determined to be patentable.

3. The method of claim 1 wherein [said] one surface of the second lens is inserted to extend proximate said first lens and intermediate the cornea and said first lens.

8. The method of claim 7 wherein said second lens consists of one of the following:
  i) collamer,
  ii) [silicon] *silicone*,
  iii) acrylic material,
  iv) synthetic resin.

10. The method of claim 1 wherein [said first and second lens each have haptics attached thereto,] said maneuvering of the second lens *is* effected to position the haptics of the second lens in generally perpendicular superimposed relation to the haptics of the first lens.

*12. The method of providing corrected vision in an eye wherein a first artificial lens including haptics has been previously placed in the lens capsule of the eye, which includes:*

*a) providing a second artificial lens to have opposed surfaces, the second lens also having haptics,*

*b) and inserting said second lens in an eye chamber forward of said capsule and generally rearward of the eye iris and pupil area so that one of said opposed surfaces faces toward said first lens, and so that the second lens remains rotatable relative to the first artificial lens,*

*c) the second lens characterized as correcting for optical defects associated with the first lens,*

*d) each lens having an associated diopter characteristic, and including the step of rotating the inserted second lens relative to the first lens into a position such that the second lens haptics are out of alignment with the first lens haptics, wherein the combined diopter characteristics of the two lenses produce good vision.*

\* \* \* \* \*